US00RE34327E

United States Patent [19]

Kreamer

[11] E Patent Number: Re. 34,327

[45] Reissued Date of Patent: Jul. 27, 1993

[54] INTRALUMENAL GRAFT

[76] Inventor: Jeffry W. Kreamer, 154 Woodstone Dr., Buffalo Grove, Ill. 60089

[21] Appl. No.: 509,162

[22] Filed: Mar. 23, 1990

Related U.S. Patent Documents

Reissue of:

[64] Patent No.: 4,740,207
Issued: Apr. 26, 1988
Appl. No.: 905,490
Filed: Sep. 10, 1986

[51] Int. Cl.[5] ..... A61F 2/06
[52] U.S. Cl. ..... 623/1
[58] Field of Search ..... 606/151, 153–155, 606/191, 194, 198; 623/1, 12

[56] References Cited

U.S. PATENT DOCUMENTS 3,975,371 8/1976 Lednicer et al. ..... 534/879
4,451,256 5/1984 Weikl et al. ..... 128/343 X
4,577,637 3/1986 Mueller, Jr. ..... 128/658
4,617,932 10/1986 Kornberg ..... 623/1 X

*Primary Examiner*—Randall L. Green
*Assistant Examiner*—Gina M. Gualtieri
*Attorney, Agent, or Firm*—Kent A. Herink; Brian J. Laurenzo

[57] ABSTRACT

An intralumenal graft for the repair of damaged or weakened sections of the vascular system. The graft consists of a semi-rigid, resilient tube made of a material suitable for long-term residence inside a vessel. The tube has a relaxed, smaller diameter and is expandable to a larger diameter which is maintained by a retaining ledge or teeth on the inside of the graft. Repair of a vessel is attained by insertion of the graft in its relaxed condition into the vessel at a site which may be remote from the damaged section. The graft is positioned and expanded to its larger diameter by a balloon catheter. Once expanded, the graft is retained in position by friction with the inner wall of the vessel.

10 Claims, 2 Drawing Sheets

INTRALUMENAL GRAFT

Matter enclosed in heavy brackets [ ] appears in the original patent but forms no part of this reissue specification; matter printed in italics indicates the additions made by reissue.

BACKGROUND OF THE INVENTION

The invention relates generally to intralumenal grafts and, more particularly, to prosthetic grafts to assist in the repair of diseased or damaged sections of a vessel.

A common health problem is diseased or damaged blood vessels which may either weaken and rupture or which become partially or wholly occluded by atherosclerotic plaque. Substantial injury and often death can result from the hemorrhaging at the site of a ruptured blood vessel. Strokes, for example, are frequently caused by the rupture of either intracerebral or extracerebral arteries wherein paralysis or death is caused by hemorrhaging into the brain or its surrounding structures. Atherosclerotic lesions are the leading cause of coronary heart disease. The repair of coronary arteries with atherosclerotic lesions is the purpose of coronary artery bypass surgery.

Conventional methods for repairing diseased and occluded sections of arteries includes invasive surgery to expose to a surgeon the section of the artery to be repaired. The section having the lesion is resected and replaced by a section of artery removed from a remote site of the patient's vascular system or by a prosthetic tubular graft. This prior art technique is traumatic to the patient, requires major surgery, and frequently may be difficult to perform because of the frequently very poor health of the patient. A second prior art technique utilizes a balloon catheter which is inserted into the artery and fed up to the site of the atherosclerotic lesion. The balloon is expanded and the atherosclerotic plaque compressed thereby increasing the size of the artery. Balloon catheter repairs are not always effective and even successfully opened arteries will require additional treatment within a period ranging from months to three years.

SUMMARY OF THE INVENTION

The present invention consists of an intralumenal graft for the repair of damaged or weakened sections of the vascular system. The graft is formed of a generally rectangular section of a semi-rigid material suitable for long-term residence within the vessel. The rectangular section is rolled so that an inside longitudinal edge is overlapped by the opposite longitudinal edge. In its relaxed state, the graft is generally cylindrical having a relatively small diameter and a cross section which is a section of a spiral. The generally cylindrical graft can be expanded from its smaller diameter to a larger diameter by partially unrolling the cylinder, with the result that the cross section is now a shorter section of a spiral having a larger inner and outer diameter. The inner surface of the rectangular section includes a retaining means which acts to restrain the expanded graft from returning to its relaxed, smaller diameter condition.

To repair a section of a vessel, the graft in its relaxed, smaller diameter condition is inserted into the vessel and positioned appropriately as the application and conditions demand. The graft is then expanded to a larger diameter, somewhat greater than the inner diameter of the vessel. The retaining means prevents the gratt from returning to its relaxed, smaller diameter. Friction between the outer periphery of the graft and the inner periphery of the vessel prevent displacement of the graft once in place in the vessel. The invention may be used alone to form a prosthetic graft which extends across the diseased or weakened section onto healthy sections of the vessel, or may be used in shorter lengths as retraining rings to hold in position a conventional tubular [grafr] *graft.*

DETAILED DESCRIPTION OF A PREFERRED EMBODIMENT

Figure 1:
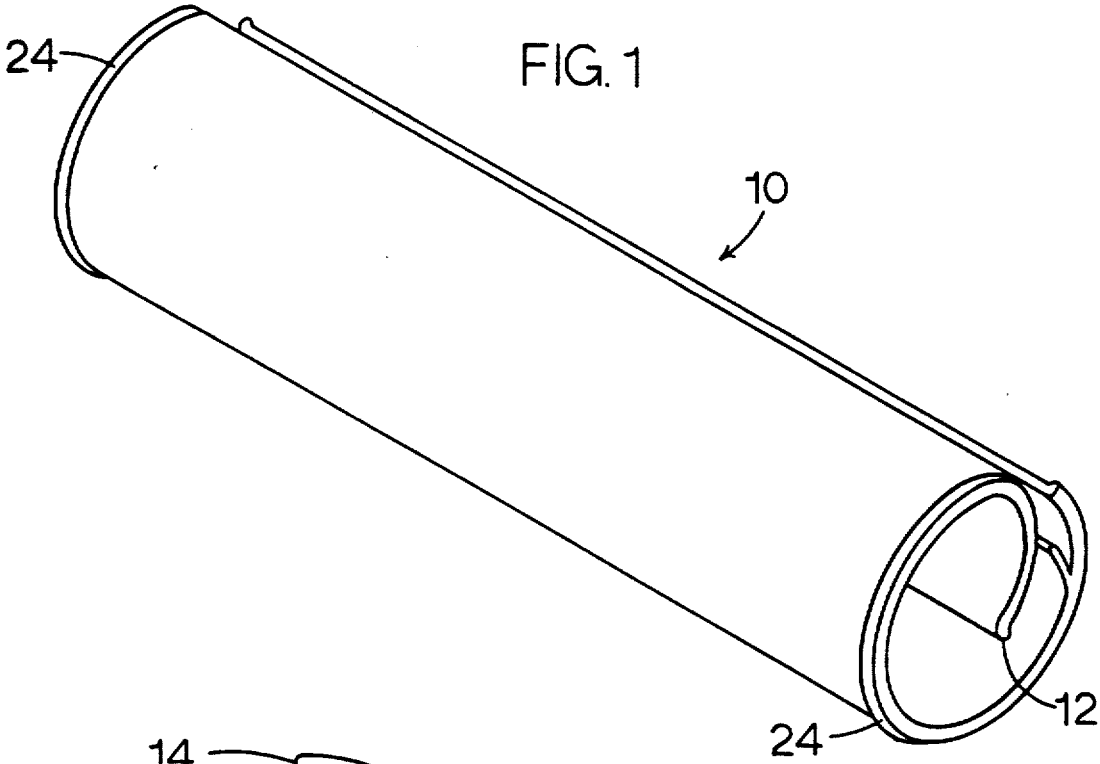
FIG. 1 is a perspective view of an intralumenal graft of the present invention.

In FIG. 1 is illustrated an intralumenal support or graft of the present invention, generally at 10, shown in a relaxed, smaller diameter condition. The graft 10 is generally cylindrical, being comprised of a rolled, generally rectangular section of a semi-rigid material. As the graft will be inserted into a blood vessel where it may remain for extended periods of time, the material used to manufacture the graft 10 should be substantially inert or non-reactive for long periods of time. Plastic of a suitable resiliency and rigidity is coated with a reduced friction compound, such as Gore-Tex® (polytetrafluoroethylene), in a preferred embodiment. Additionally, encapsulated or embedded prostacyclenes can be added to give a long term anti-coagulent or anti-platelet effect to the graft.

Figure 2:
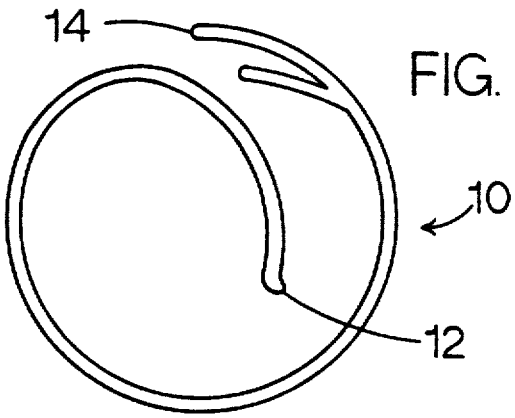
FIG. 2 is an end view of a graft in its relaxed, smaller diameter condition.

The graft 10 is illustrated in a relaxed, smaller diameter condition, in FIG. 2. The cross-section of the graft 10 forms a spiral which begins at an inner, longitudinal edge 12 and spirals outwardly to an outer, longitudinal edge 14. In this relaxed, smaller diameter condition, an expansile force is required to increase the diameter of the graft 10. That is, the material comprising the graft 10 is resilient and will attempt to return to its relaxed condition as illustrated in FIG. 2 unless restrained.

Figure 3:
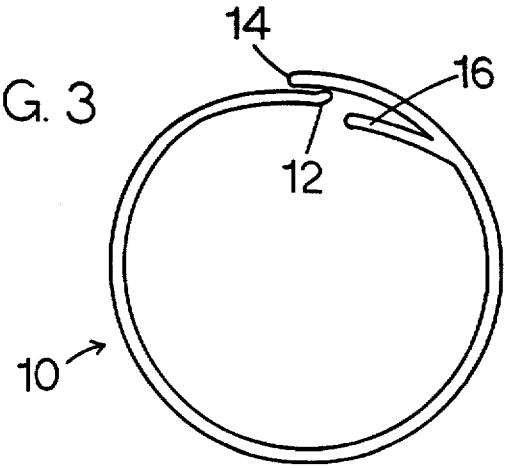
FIG. 3 is an end view of the graft in a maximum, larger diameter condition.
Figure 5:
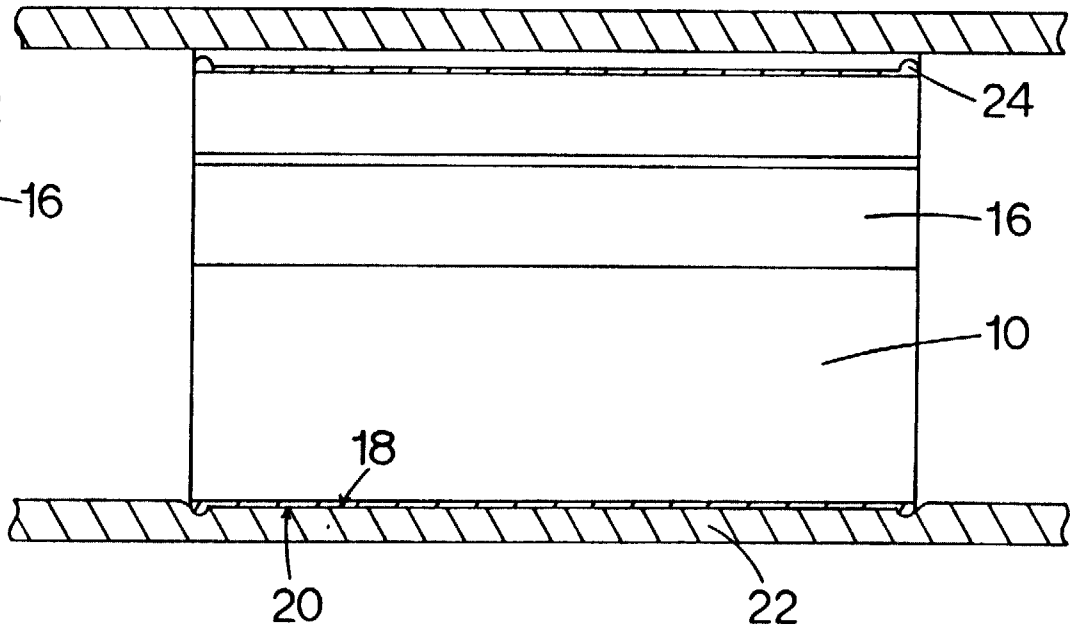
FIG. 5 is a cross-sectional view taken along the line 5—5 of FIG. 4.
Figure 4:
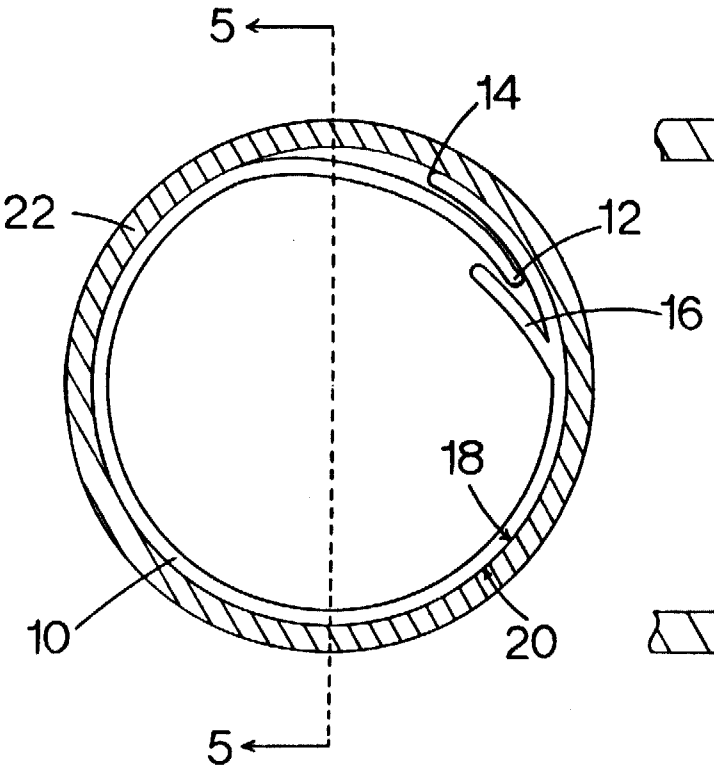
FIG. 4 is an end view of the graft in an expanded, larger diameter condition in place inside a vessel.

If an expansile force is exerted on the interior of the graft 10 in its relaxed condition (FIG. 2), it will unroll, thereby increasing its outer diameter. A maximum diameter condition is illustrated in FIG. 3. The graft 10 has been expanded until the inner edge 12 is nearly adjacent but still inside the outer edge 14. Note that the inner edge 12 has moved past a retaining means or inwardly projected tooth member 16. If the expansile force is now released, the resiliency of the graft 10 will cause it to move towards its relaxed, smaller condition. As is illustrated in FIG. 1 and FIG. 4, the inner edge 12 will be restrained by the tooth member 16 and the graft 10 will be held in an expanded position or diameter defined by the circumferential distance from the inner edge 12 to the base of tooth member 16. Of course, the tooth member may alternatively be placed on the outer periphery of the graft. The edge of the graft that is trapped or restrained is now an "outer" edge in that it is the longitudinal edge of the graft that is on the outside of the graft in its relaxed condition. The description of the graft and its use, as discussed below, is identical in all other respects.

Repair of a damaged section of a vessel proceeds by insertion of the graft in its relaxed, smaller diameter condition into the vessel. The site of insertion of the graft into the vessel may be remote from the site of the section requiring repair. For example, if a coronary artery having an atherosclerotic lesion is to be repaired, the graft may be initially inserted into the aorta downstream of the locus of the arteriostenosis. The graft is then moved into the appropriate position by suitable means, such as a catheter on which the graft may be carried through the vessel. A radio-opaque indicator may be marked on the graft to facilitate accurate positioning of the graft within the vessel.

Once the graft has been appropriately positioned, an expansile force is exerted within the interior of the graft to expand it to a larger diameter. After the diameter has been expanded so that the inner edge 12 is beyond the tooth member 16 but inside the outer edge 14, as illustrated in FIG. 3, the expansile force may be removed and the graft allowed to coil to the final, expanded condition as illustrated in FIG. 4. Suitable means for applying an expansile force include a conventional balloon catheter having a balloon at the proximal end of the catheter used to position the graft. Inflation of the balloon will exert the expansile force and thereby uncoil the graft.

The final, expanded diameter of the graft is chosen so that the outer diameter of the graft in such condition places the outer periphery of the graft in contact engagement with the inner periphery of the vessel being repaired. FIG. 4 illustrates the graft 10 in position inside a vessel 22 wherein the outer periphery 18 of the graft is in contact engagement with the inner periphery 20 of the vessel 22. This contact engagement of the graft 10 and the vessel 22 will prevent movement of the graft 10 within the vessel 22 after it has been positioned and expanded to its final condition. The contact engagement also prevents blood which circulates within the vessel from seeping between the graft 10 and the vessel 22 so that it is contained away from the damaged or weakened section. Assisting in the contact engagement and sealing of the graft 10 is a raised lip 24, best illustrated in FIG. 1, at each end of the graft 10. The raised lip 24 will generally extend radially by an amount proportional to the inner diameter of the vessel being repaired, and may be proportionately larger or smaller than that illustrated depending on the conditions and application.

The intralumenal graft and method of arterial repair is also effective for the treatment of other types of arteriostenosis. In particular, renal arteriostenosis caused by renal artery muscular hypertrophy can be treated by the insertion of a graft of this invention having a stiffness sufficient to resist the forces exerted by the hypertrophied muscle.

The invention can also be practiced in association with a conventional tubular prosthetic graft as a means of anchoring the graft in position inside the vessel. The graft is foreshortened into a ring-shaped configuration and its outer periphery is secured to the inner periphery of the graft. When positioned and expanded within the vessel, the ring-shaped graft will hold the tubular graft at the desired location. A plurality of ring-shaped grafts can be used to anchor the tubular graft at a number of points. This use of the present invention would be particularly applicable to the aneurysm repair method of U.S. Pat. No. 4,577,631. The intralumenal grafts may also be inserted in an end-to-end relationship to cover large sections or to treat curved sections of artery.

I claim:

1. An intralumenal support for insertion into a [damage] *damaged* section of a vessel, comprising:

(a) a graft element formed of a rolled, generally rectangular section of a resilient material suitable for [long term] residence inside the vessel and expandable substantially uniformly over its entire length from a relaxed, small diameter to one or more larger diameters;

(b) retaining means on said graft element;

(c) a first, generally longitudinal edge of said graft element and;

(d) a second, generally longitudinal edge of said graft element which, when said graft element is at its relaxed diameter, is inside said retaining means and said first edge, wherein (e) upon expansion of said graft element from said relaxed, small diameter to one or more larger [diameter] *diameters*, said [first] *second* edge is retained by said retaining means which thereby prevents said graft element from returning to the smaller diameter.

2. The support as defined in claim 1, wherein:

(a) the section of. [th evesel] *the vessel* admits of repair over a length bounded on either end by a healthy section of the vessel;

(b) said support is of a length at least equal to said length of the section admitting of repair to extend onto said healthy sections of the vessel.

3. The support as defined in claim 1, wherein:

(a) said retaining means is an inwardly extended projection that curves toward said second edge.

4. The graft as defined in claim 1, wherein:

(a) said resilient material includes an outer coat of a reduced friction compound.

5. The graft as defined in claim 1, wherein:

(a) said resilient material has an anticoagulent effect.

6. The graft as defined in claim 1, wherein:

(a) said resilient material resists the formation of atherosclerotic plaque.

7. The graft as defined in claim 1, further comprising:

(a) a radio-opaque indicator(s) on said graft element to assist in radiographic location of the graft inside the vessel.

8. The graft as defined in claim 4, wherein:

(a) said reduced friction compound is a polytetrafluoroethylene compound.

9. The support as defined in claim 1, wherein:

(a) the damaged section of the vessel is occluded at least partially by [atheriosclerotic] *atherosclerotic* plaque; and (b) said graft in its expanded diameter opens said vessel to reduce said occlusion.

*10. An intralumenal support as defined in claim 1 wherein the graft is suitable for long term residence.*

* * * * *